United States Patent
Queiroz Ferreira

(10) Patent No.: US 10,813,970 B2
(45) Date of Patent: Oct. 27, 2020

(54) **PHARMACEUTICAL COMPOSITION ON THE BASIS OF *STACHYTARPHETA* SP., A PROCESS FOR OBTAINING THE SAME AND ITS USE FOR TREATING VITILIGO**

(71) Applicant: ACHE LABORATORIOS FARMACEUTICOS S/A, Guarulhos, SP (BR)

(72) Inventor: Emerson Queiroz Ferreira, Sao Paulo (BR)

(73) Assignee: Aché Laboratórios Farmacêuticos S.A., Sao Paulo (BR)

( * ) Notice: Subject to any disclaimer, the term of this patent is extended or adjusted under 35 U.S.C. 154(b) by 0 days.

(21) Appl. No.: 15/815,964

(22) Filed: Nov. 17, 2017

(65) Prior Publication Data
US 2018/0071356 A1   Mar. 15, 2018

Related U.S. Application Data

(62) Division of application No. 12/527,242, filed as application No. PCT/BR2007/000316 on Nov. 14, 2007, now abandoned.

(30) Foreign Application Priority Data

Feb. 15, 2007 (BR) .............................. PI0700767-1

(51) Int. Cl.
*A61K 36/85* (2006.01)
*A61K 31/352* (2006.01)

(52) U.S. Cl.
CPC ............ *A61K 36/85* (2013.01); *A61K 31/352* (2013.01)

(58) Field of Classification Search
CPC .................................................... A61K 36/85
See application file for complete search history.

(56) References Cited

U.S. PATENT DOCUMENTS

| | | |
|---|---|---|
| 7,402,669 B2 | 7/2008 | Loiseau et al. |
| 2001/0024809 A1 | 9/2001 | Minghetti et al. |
| 2003/0175366 A1 | 9/2003 | Pauly et al. |
| 2004/0077556 A1 | 4/2004 | Chinery |
| 2006/0293257 A1 | 12/2006 | Rosenbloom |
| 2010/0028400 A1 | 2/2010 | Ferreira |
| 2018/0071357 A1 | 3/2018 | Ferreira |
| 2019/0134136 A1 | 5/2019 | Emerson |

FOREIGN PATENT DOCUMENTS

| | | |
|---|---|---|
| BR | PI0406343 A | 8/2006 |
| BR | PI0700767 | 9/2008 |
| EP | 1118617 A1 | 7/2001 |
| EP | 1145709 A1 | 10/2001 |
| EP | 1736167 | 12/2006 |
| EP | 2117533 | 12/2014 |
| JP | 8268844 A | 10/1996 |
| JP | 2006516962 | 7/2006 |
| JP | 5443174 | 3/2014 |
| WO | WO 2007/098873 | 9/2007 |
| WO | WO 2008/098325 A1 | 8/2008 |

OTHER PUBLICATIONS

Neto et al, "Recursos medicinais de especies do cerrado de Mato Grosso: um estudo bibliografico," Acta Botanica Brasilica, vol. 17, No. 4, pp. 561-584 (Year: 2003).*

Schapoval E.E. et al.,"Antiinflammatory and antinociceptive activites of extracts and isolated compunds from Stachytarpheta cayennensis", Journal of Ethnopharmacology (1998), 60(1), pp. 53-59; abstract (1998:83076; HCAplus).

Cappuccino N. et al., "Novel chemistry of invasive exotic plants", Biology Letters 2006, 2(2), pp. 189-193; abstract (2006:750915; HCAp/us).

Spritz, "The Genetics of Generalized Vitiligo," Dermatologic Immunity, Curr Dir Autoimmun, Basel, Karger, vol. 10, pp. 244-257 (2008).

Taieb et al, "Targeting iHSP 70 in Vitiligo: a Critical Step for Cure?," Experimental Dermatology, vol. 22, No. 9, pp. 570-571 (2013).

Agmon-Levin et al, "Prediction and Prevention of Autoimmune Skin Disorders," Archives of Dermatological Research, vol. 301, No. 1, pp. 57-64 (2009).

Raintree Nutrition, Inc., "Database File for: Gervao (Stachytarpheta sp)," available at <<http://www.raintree.com/gervao.htm>> (webpage captured on Oct. 17, 2006) (8 pages)).

Akaike et al., Collection of Pharm Soc of Japan Annual Convention Gists, 2002, 122(2): 128.

EP Supplementary European Search Report in European Appln. No. 07815757.5, dated Jul. 1, 2010, 3 pages.

EP Supplementary European Search Report in European Appln. 07815757, dated Jun. 23, 2010, 2 pages.

Giovannelli et al., "Increased oxidative DNA damage in mononuclear leukocytes in vitiligo," Mutation Research, 2004, 556: 101-106.

Guimaraes et al., "Step-gradient CCC separation of phenylpropanoid in iridoid glycosides from roots of *Stachytarpheta cayennensis* (Rich.) vahl," J Liquid Chromatography and Related Tech, Jan 2005, 28(12-13): 2053-2060.

(Continued)

*Primary Examiner* — Dennis J Parad
(74) *Attorney, Agent, or Firm* — Fish & Richardson P.C.

(57) ABSTRACT

This invention generally refers to the process to obtain a compound and a standard pharmaceutical product from one or more parts of plants of the *Stachytarpheta* (Verbenaceae family) species, as well as roots, stems, barks, and leaves of plants in the form of extracts or enriched fractions, or pure isolated compounds or compounds obtained from synthesis, used alone or mixed with other natural or synthetic products, in different ratios, in order to integrate pharmaceutical compositions to be used by appropriate routes (topic or oral), particularly in the form of tablets, capsules, dyes, emulsions, W/O and O/W (creams and gels), liposomes, microcapsules, nanoparticles, aerosols, ointments, and the like, as well as formulations for slow-release implants, used to treat vitiligo.

13 Claims, No Drawings

(56) References Cited

OTHER PUBLICATIONS

JP Notification of Reasons for Refusal in Japanese Appln. No. 2009-549340, dated Nov. 27, 2012, 7 pages. (English translation).
Neto et al., "Recursos Medicinais de especies do cerrado de Mato Grosso: um estudo bibliografico," Acta Botanica Brasillica, 2003, 17(4):561-584 (English abstract).
PCT International Preliminary Report on Patentability in International Appln. No. PCT/BR2007/000316, dated Aug. 19, 2009, 4 pages.
PCT International Search Report in International Appln. No. PCT/BR2007/000316, dated Jun. 30, 2008, 4 pages.
PCT Written Opinion in International Appln. No. PCT/BR2007/000316, dated Jun. 30, 2008, 3 pages.

* cited by examiner

PHARMACEUTICAL COMPOSITION ON THE BASIS OF *STACHYTARPHETA* SP., A PROCESS FOR OBTAINING THE SAME AND ITS USE FOR TREATING VITILIGO

CROSS REFERENCE TO RELATED APPLICATIONS

The present application is a divisional of U.S. patent application Ser. No. 12/527,242, filed on Sep. 18, 2009, which is a U.S. National Phase Application under 35 U.S.C. § 371 of International Patent Application Serial No. PCT/BR2007/000316, filed on Nov. 14, 2007, which claims priority to Brazilian Patent Application Serial No. PI0700767-1, filed on Feb. 15, 2007, each of which are hereby incorporated by reference in their respective entirety herein.

This invention generally refers to the obtention of a compound and a standard pharmaceutical product from roots, stems, barks, and leaves of plants of the *Stachytarpheta* (Verbenaceae family) genus, in the form of extracts or enriched fractions, or pure isolated compounds or compounds obtained from synthesis or semi-synthesis, used alone (pure extract) or mixed with other natural or synthetic products, in different ratios, in order to integrate pharmaceutical compositions to be used by appropriate routes (topic or oral), particularly in the form of tablets, capsules, dyes, emulsions, W/O and O/W (creams and gels), liposomes, microcapsules, nanoparticles, aerosols, ointments, and the like, as well as formulations for slow-release implants, used to treat vitiligo and manifestations thereof—loss of skin pigment.

BASIS OF THE INVENTION

The name vitiligo was used for the first time by the Roman physician Celsus (50 a. C). It originates from the Latin word vitilus, which means white patch. The descriptions of such disease were recorded in the Ebers Papyrus (1500 b.C), and in the Hindu sacred book Anthe (1400 b.C), where it is called Schwetakustha.

Vitiligo is a disease characterized in that the skin patches that may appear in several body parts, mainly arms, legs, mouth, and eyes. In all cases, the melanin is observed to disappear. The vitiligo occurs by the destruction of melanocytes, however the cause is not completely clear. There are four theories suggested for the development of vitiligo: autoimmune, self-destructive, neurogenic and mixed therapy.

| | |
|---|---|
| Autoimmune | This theory is based on the association of immunological factors, just like other diseases of immunological origin, such as Hashimoto's thyroiditis. |
| Neurogenic | This theory suggests that the release of components produced by the nervous stimuli may inhibit the production of skin melanin. |
| Self-Destructive | It suggests that the melanocytes are destroyed by flaws in the protective mechanism that removes the chemical toxins generated by the melanogenesis. |
| Mixed | This theory takes into account the possibility of gathering all the lines described above. |

Vitiligo is considered an autoimmune disease, presented as a melanocyte-specific immunological and multifactorial disease of endogenous origin: genetics and melanocitary oxidation or of exogenous origin: rubbing, skin lesions (Köebner Phenomenon).

Recent researches have demonstrated the existence of specific biochemical failures on the catalase activity and an accumulation of hydrogenated peroxide in the skin of vitiligo patients. The catalase suggests that keratinocytes in vitiligo are capable of recycling the 5, 6, 7, 8-tetrahydrobiopterin (6-BH$_4$), an adjuvant factor for the hydroxylation of L-phenylalanine into L-tyrosine. This may break the supply of L-thyroxine for the melanin production, increasing the catecholamine by the keratinocytes, resulting in the accumulation of toxic free radicals that may damage the melanocytes.

Morphologically, regarding the occurrence of discolored areas, the vitiligo may occur in eight forms:

| | |
|---|---|
| Symmetrical | The most common discoloration form, developed in both sides of the human body. |
| Asymmetrical | Affects one side of the body only. |
| Segmentary | Follows the path of one nerve. |
| Cicrumscript | Affects the pigmentation of a small area only. |
| Universal | Appears around dark, pigmented patches. |
| Congenital | Is the unpigmented form of vitiligo that occurs from the birth. |
| Generalized | Affects the skin almost in its entirety. |
| Ocular | Affects the retina, causing pain and photophobia. |

The available treatments are:

Psychological: it is necessary to face vitiligo with simplicity. Since it is a psychological disease, the treatment shall not be considered before the patient believes that he/she is capable of recovery.

Use of melagenine: it helps decreasing the patches in 75% of the patients.

Use of Diprosalic: Diprosalic solution, less efficient than melagenine, is topically used on the patches.

Use of sun protection factors: used across all treatment variations. Sun burnt leads to a potential photocarcinogenesis and may broaden unpigmentation areas (Köebner Phenomenon).

Use of topical corticosteroids: Used for small vitiligo patches with response after weeks or months. One of the most powerful includes betamethasone and clobetasol propionate. The follow-up on a monthly or bimonthly basis guarantees the control of side effects, such as spider veins, acne and skin atrophy. Upon any sign of those effects, the intermittent use shall be avoided. The treatment outcomes must be observed within three months, taking into account that those are immunosupressor drugs.

PUVA: The most usual vitiligo treatment is the photochromotherapy associated to psoralen, usually 8-methoxypsoralen (8-MOP), and artificial exposure to a 315-400 nm fluorescent lamp for approximately 10 minutes. The pigmentation may occur gradually in a perifollicular manner (around the hair follicle), although a few cases it acts over the whole area. If no response is achieved within three months, the treatment must be discontinued. In case of repigmentation responses, it may be applied for one to one and a half year, always with approximately 2-month resting intervals, since these drugs are considered hepatotoxic, nephrotoxic and cause gastric and ocular disorders. To avoid the risk of photocarcinogenesis, the treatment shall be administered with 100 to 150 expositions. Only 30% of the patients who underwent the PUVA therapy achieved a good repigmentation, and among them, approximately 75% relapsed within 2 to 3 years.

In light of the foregoing, it was demonstrated that the existing treatments are not satisfactory to fight vitiligo manifestations. It is important to use efficient and safe drugs for both treatment and prophylaxis, especially natural drugs and low toxicity drugs. Those natural products must comprise pharmaceutical formulations to be used by the appropriate routes.

Yet on the prior art, the document PI 0406343-0 relates to the use of aqueous, hydroalcoholic, alcoholic or organic solvents extracts from leaves and/or aerial parts of the *Stachytarpheta polyura* species, used to treat vitiligo. This species, *Stachytarpheta polyura*, is rarely found in nature, and its diminutive size makes the production of the extract in industrial scale unfeasible, costly and unprofitable.

OBJECTIVES OF THE INVENTION

Therefore, and due to this invention, it has just been scientifically proven, through laboratory pre-clinical tests regarding toxicological and pharmacological assessments—both in vitro and in vivo, followed by clinical evaluations with a significant number of patients—using alcoholic, hydroalcoholic and aqueous extracts from one or more parts of plants of one of the *S. cayennensis, S. jamaicensis* and *S. elatior* species, or a mixture of them, that this invention is composed of powerful therapeutic agents, whether alone or mixed in different ratios with each other or with other products, whether natural or synthetic, capable of fighting vitiligo, according to the data and results described below.

Our researches were initially carried out using data obtained by ethnopharmacological assessments on plants used by the Brazilian popular medicine, empirically known to present repigmentation properties that fight vitiligo. Then the phytochemical, pharmacological and toxicological studies were carried out using alcoholic, hydroalcoholic and aqueous extracts from the aerial parts of more than 30 plants, including several species of the *Stachytarpheta* genus. Through those screenings, it was found that both the decoction and the hydroalcoholic extract from the *S. cayennensis, S. jamaicensis* and *S. elatior* leaves present cicatrizant and anti-inflammatory pharmacological activities. These data corroborate with the use of verbena by the domestic medicine. The analyses of the results have also demonstrated that the referred extracts do not present cytotoxicity when assessed in micro-larvae of *Artemia salina*; neither relevant toxicity, when assessed against alevins of *Poecilia reticulata* and mice. Through the microbiological, antibacterial and antifungal in vitro assessment, carried out with different concentrations, a modest antimicrobial activity is observed.

The newly developed product may be synthesized, semi-synthesized or obtained from alcoholic, aqueous or hydroalcoholic or organic extracts from one or more parts of plants of one of the following species, or a mixture thereof: *S. cayennensis, S. jamaicensis* and *S. elatior*.

The species used in this invention are more easily found in nature than *Stachytarpheta polyura*, mentioned on the prior art, in larger quantities, as well as larger sizes, increasing the feasibility of the production in industrial scale. Such species, popularly known as gerbão, gerbão, overjão, chá-do-Brasil ("verbena/vervain"), among other popular names, are used in the traditional medicine as cicatrizant, treatment for stomach problems and antifebrile.

The new pharmaceutical invention uses pure extracts, synthetic or semi-synthetic compounds or isolates from those plants' extracts, whether alone or mixed with each other or yet associated to extracts, fixed oils, essential oils, fragrances, powders or excipients from other natural or synthetic sources.

Through pre-clinical and clinical tests, it has been proven that the identified compounds are used as part of medications formulas to treat vitiligo, used by oral route when in tablets or capsules, and by topical route as dyes, creams, gels, aerosols or similar others used as adjuvant. This invention also extends to the pharmaceutical compositions containing, besides the referred extracts, fractions or components of those extracts (natural or synthetic), used to formulate medications applied on the treatment or prophylaxis of vitiligo.

DESCRIPTION OF THE INVENTION

In the first aspect, this invention is about a process to produce a pharmaceutical product from standardized extracts, fractions or isolate molecules from plants of the *Stachytarpheta* genus, *S. cayennensis, S. jamaicensis* and *S. elatior* species of the Verbenaceae family, to be used as a medication to treat vitiligo. The production process according to this invention is comprised of the following stages:

(a) The biomass that forms one or more parts, whether green or dried, of the plant, roots, stems, barks and leaves of the species of *Stachytarpheta* genus, is pulverized, or ground, or chopped, or crumbled, considering that the raw material may be comprised, with no limitation, of the *S. cayennensis, S. jamaicensis* or *S. elatior* species or their mixtures;

(b) The biomass obtained through the process (a) is extracted by percolation, or maceration, or soxlhet, or using gases in supercritical state, or extraction using a base or acid medium or an organic solvent or extraction by steam distillation; considering that the organic solvents are, for example, halogenated compounds, alcohols, aldehyde, ketones, cycloalkanes or alkanes, phenolic compounds, benzenes and derivatives, among other, whether alone or their mixtures; and in the case of an acid/base extraction, the extraction may be performed with strong or weak acids, whether diluted or concentrated, alone or mixed, such as acetic acid, hydrochloric acid, formic acid; and the base used in the extraction process is formed by concentrated or diluted bases, whether alone or in mixtures, such as, for example, ammonium hydroxide ($NH_4OH$) and sodium carbonate ($Na_2CO_3$);

(c) The extract obtained may be dried using spray-dryer, with inlet temperature of approximately 150-190° C., and outlet temperature of approximately 60-90° C.; or under reduced pressure, with temperature ranging between 25-75° C.; or at room temperature. The process, according to this invention, allows the production in industrial scale, since it reduces the process time, presents an appropriate yield and results in a pharmaceutical product. The medication, according to this invention, contains around 0.001 to 99% of at least one of the compounds or their mixtures in free form or in salt form (such as chlorates, sulfates or borates) of chemical structure (I), (II), (III), (IV), (V), (VI) and (VII).

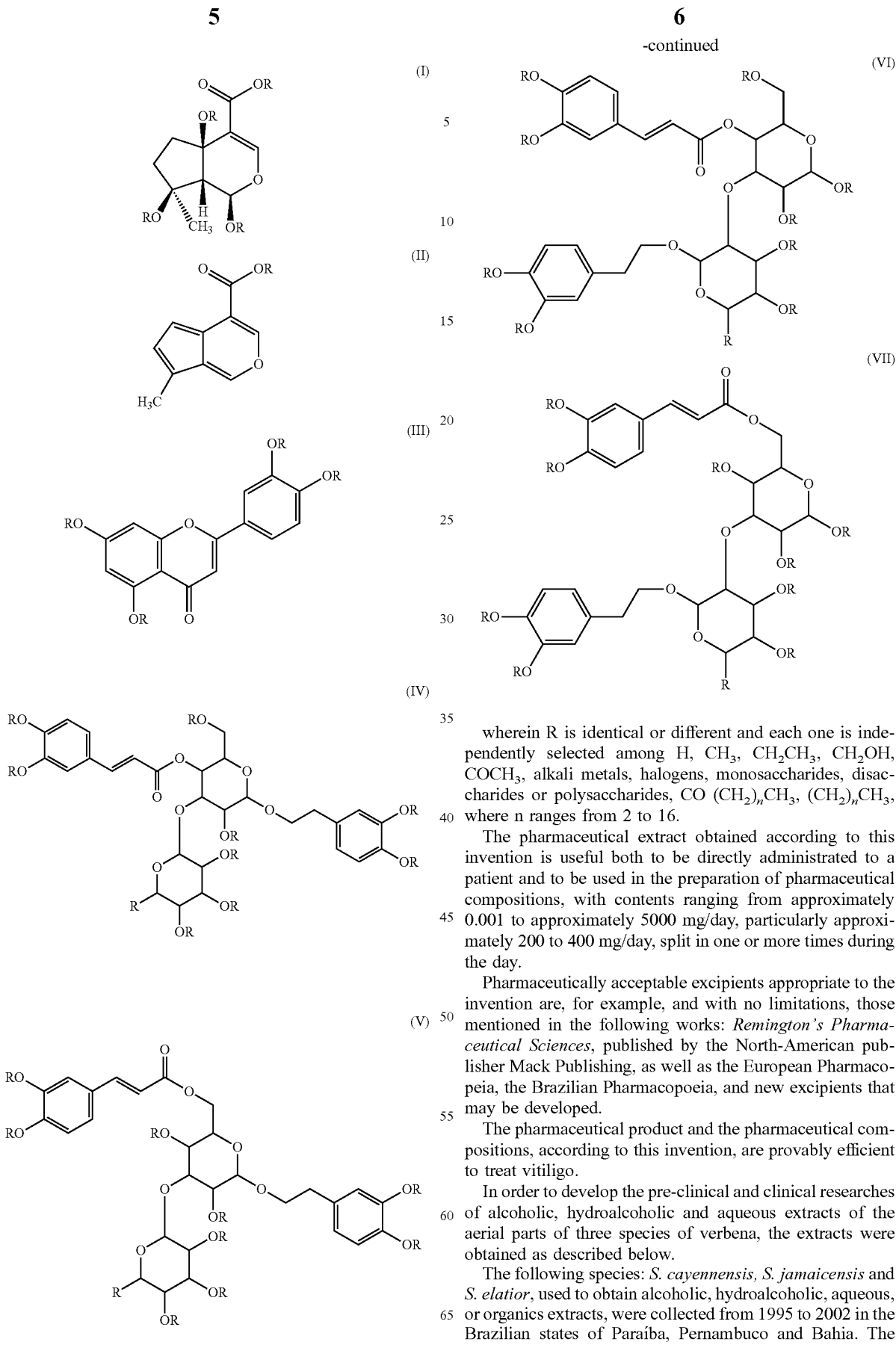

wherein R is identical or different and each one is independently selected among H, $CH_3$, $CH_2CH_3$, $CH_2OH$, $COCH_3$, alkali metals, halogens, monosaccharides, disaccharides or polysaccharides, $CO(CH_2)_nCH_3$, $(CH_2)_nCH_3$, where n ranges from 2 to 16.

The pharmaceutical extract obtained according to this invention is useful both to be directly administrated to a patient and to be used in the preparation of pharmaceutical compositions, with contents ranging from approximately 0.001 to approximately 5000 mg/day, particularly approximately 200 to 400 mg/day, split in one or more times during the day.

Pharmaceutically acceptable excipients appropriate to the invention are, for example, and with no limitations, those mentioned in the following works: *Remington's Pharmaceutical Sciences*, published by the North-American publisher Mack Publishing, as well as the European Pharmacopeia, the Brazilian Pharmacopoeia, and new excipients that may be developed.

The pharmaceutical product and the pharmaceutical compositions, according to this invention, are provably efficient to treat vitiligo.

In order to develop the pre-clinical and clinical researches of alcoholic, hydroalcoholic and aqueous extracts of the aerial parts of three species of verbena, the extracts were obtained as described below.

The following species: *S. cayennensis*, *S. jamaicensis* and *S. elatior*, used to obtain alcoholic, hydroalcoholic, aqueous, or organics extracts, were collected from 1995 to 2002 in the Brazilian states of Paraíba, Pernambuco and Bahia. The foliorum exsiccata of the specimens were individually stored in the files of Herbário Lauro Pires Xavier, Universidade Federal da Paraíba, city of João Pessoa, Brazil.

The alcoholic extracts of the leaves and aerial parts of the plants were individually extracted through percolation, using ethanol as solvent, during 72 to 144 hours in a row.

After the extraction and concentration in rotavapor, the dried extract had its weight determined, as well as its respective yield in relation to the fresh weight of the vegetable materials.

The yield of the ethanolic extracts of leaves and aerial parts per species were the following:

| Species | % Ethanolic Extract leaves | % Ethanolic Extract Aerial parts |
|---|---|---|
| S. cayensensis | 12 to 18 | 8 to 13 |
| S. jamaicensis | 11 to 16 | 7 to 13 |
| S. elatior | 11 to 19 | 7 to 14 |

The aqueous extracts of the leaves and aerial parts of the plants were individually extracted through decoction, using water as solvent, during 72 to 144 hours in a row. After the extraction and concentration in rotavapor, the dried extract had its weight determined, as well as its respective yield in relation to the fresh weight of the vegetable materials. The average yield of the three aqueous extracts of the studied species (individually) presented the following yields: *S. cayensensis:* 12% (leaves) and 11% (aerial parts); *S. jamaicensis:* 14% (leaves) and 12% (aerial parts) and *S. elatior:* 11% (leaves) and 9% (aerial parts). The partitions (liquid-liquid) of those extracts were carried out using solvents, in increasing order of polarity with hexane, chloroform, butanol and water, which were evaporated in rotavapor under reduced pressure.

The purification of the aqueous extracts of the leaves and aerial parts of the plants was carried out with 10 g of the aqueous extract by CMP, using in the eluent system a mixture of MeOH and $H_2O$ with 0.05% of trifluoroacetic acid (TFA) in gradient mode (5% to 100% in 3 days). The products were detected by UV at 254 nm. Forty fractions were obtained from this first purification stage. The fraction No. 12 (400 mg) was purified by CLHP preparation scale using a Symmetry® column (7 μm, 19×150 mm, Waters, MeOH/$H_2O$ 3:97/TFA 0.05%, flow of 10 mL/min, UV 254 nm leading to the isolation of compounds I (300 mg, $R_t$=12 min). The fraction No. 15 leads to the isolation of the compound II (145 mg). The fraction No. 18 leads to the isolation of the compound III (80 mg). The compound IV was directly isolated from fraction No. 19. The compounds V (40 mg), VI (35 mg) and VII (5 mg) were isolated from fraction No. 21.

The chemical structures of the isolate compounds were elucidated by spectroscopic methods, including ultraviolet (UV), nuclear magnetic resonance (ID and 2D NMR), low and high resolution mass spectrometry (MS and HRMS), as well as chemical and enzyme reactions. The compounds I and II were identified as iridoids, wherein the R group may be identical or different from groups H, $CH_3$, $COCH_3$, CO $(CH_2)nCH_3$ (where n ranges from 2 to 16), halogens, monosaccharides, disaccharides or polysaccharides. The compound III was identified as a flavonoid, wherein the R group may be H, $CH_3$, $CH_2CH_3$, $CH_2OH$, $COCH_3$, CO $(CH_2)_nCH_3$ (where n ranges from 2 to 16), halogen, monosaccharide, disaccharide or polysaccharide. The compounds IV, V, VI and VII were identified as ethyl phenyl propane glycosilate derivatives, wherein the R group can be H, $CH_3$, $CH_2CH_3$, $CH_2OH$, $COCH_3$, $CO(CH_2)_nCH_3$ (where n ranges from 2 to 16), halogen, monosaccharides, disaccharides or polysaccharides.

Two types of leaves of each vegetal species were selected for those analyses: small (young) and large (adults). Using that material, the foliar humidity was determined in a round bottomed flask containing 150 mL of dry toluene, previously treated and heated to a temperature of approximately 120° C., maintained until system ebullition, followed by reading of the water volumes of the steam distillation. The average of the three foliar humidity analyses of each studied species achieved the following yields: *Stachytarpheta cayensensis:* 69% (young leaves) and 67% (adult leaves); *Stachytarpheta jamaicensis:* 68% (young leaves) and 64% (adult leaves); and *Stachytarpheta elatior* 66% (young leaves) and 64% (adult leaves).

The analyses of the percentile of the foliar waxes of each species were individually carried out on the collected and identified botanical materials. For each analysis, a 1000-mL beaker was used, in which it was added 150 g of the vegetable and, then, 500 mL of chloroform P.A. After five minutes of extraction, this was filtered in a qualitative filter paper, obtaining a chloroform extract that was concentrated in reduced pressure rotavapor. The determination of the percentile of the foliar waxes was carried out after drying it in a vacuum dryer, weighed until constant weight. This quantitative analysis, repeated three times following the same methodology, revealed that the aerial part of the studies species present the following yields of the foliar waxes: Stachytarpheta cayensensis: 0.21%; Stachytarpheta jamaicensis: 0.22%; and Stachytarpheta elatior: 0.19%.

The qualitative analyses of the foliar waxes of the three species were carried out using the extract of the waxes obtained according to the abovementioned methodology (0.1 g), after the etherification reaction with diazomethane. The compositions were assessed through a gas chromatography coupled with mass spectrometry connected to a database. To perform the analyses, each methyled material was dissolved into 5 mL of n-hexane (chromatographic), and from this solution 5 [mu]L were injected into the GC/MS system model HP-5890-series 2, with a 30-m DB1 column, packed with 100% of dimethylpolysiloxane. The carrier gas used was helium, under an initial temperature of 60° C., in a 10° C./min gradient until it reaches the temperature of 240° C., coupled with a mass spectrometer, connected to a database.

The identification of the chemical components of foliar waxes was performed through the registration of the fragmentation in the mass spectrum and its molecular weight, making a simultaneous comparison to the database against 135,000 organic compounds available in the system. The foliar waxes of the three species present the following hydrocarbonates components: dodecane, tricosane and the hexadecanoic, dodecanoic, tricosanoic and eicosanoic acids.

The evaluations of the biological activities of the alcoholic extract and its liquid-liquid partitions (hexanic, chloroformic and aqueous), all obtained from aerial parts of *S. cayennensis, S. jamaicensis* and *S. elatior*, as well as from the isolate chemical components, were carried out through in vitro laboratorial tests about the free radicals captation activities (ABTS-radical), SOD mimetic, nitric oxide synthesis and inhibition of xanthine oxidase.

The extracts of *S. cayennensis, S. jamaicensis* and *S. elatior* presented a powerful captation activity of $O_2^-$ over the hypoxanthine/xanthine system. In concentrations of about 40 μg/ml, the extracts presented inhibition of the xanthine oxidase activity and production of nitric acid on the macrofages. Among the isolate compounds, the compounds II, III and IV had an important antioxidant activity under 10 µM concentrations. The IV compound presented, by its turn, a significant activity in the assay with nitric oxide at a 10 µM concentration.

The evaluations of the biological activities of the alcoholic extract and its liquid-liquid partitions (hexanic, chloroformic and aqueous), all obtained from aerial parts of *S. cayennensis, S. jamaicensis* and *S. elatior*, as well as from the isolate chemical components, were carried out in in vivo tests, as follows: the cytotoxicity tests were carried out using alevins of *Poecilia reticulata*; the toxicity tests used larvae of *Artemia salina*, and the microbiological tests used 7 bacteria, 5 yeast-like fungi and 6 filamentous fungi.

The assays to assess for ichthyotoxic or piscicide characteristics were performed with alevins of *Poecilia reticulata*, collected from the River Jaguaribe in the city of João Pessoa—PB [State of Paraiba], acclimatized in laboratory for 48 hours, fed with fish food. The alevins used in the biological assays had an average of 17.1 mm in length. The alcoholic, hydroalcoholic and aqueous (decoction) extracts were diluted in distilled water in the concentrations of 1, 10 and 100 µg/mL.

The product solutions, in the three concentrations, were used on the biological evaluation tests in a 1000-mL beaker covered with tulle nets, containing 400 mL of the solution of each product. The assays were carried out with groups of 10 alevins, individually, with exposure time of 24 hours. During this period, the referred solutions were aired with appropriate devices under room temperature. For each biological assay, a control test in distilled and aired water was carried out with 10 alevins collected and treated likewise.

The gross evaluation of the activity of those substances about alevins was carried out by means of physiological and behavioral changes, such as: hyperactivity, convulsive movements, loss of balance, attempt to escape the bowls and death. The results revealed that the products were nontoxic in all of the three tested concentrations.

The evaluation of the cytotoxic activity of the alcoholic and hydroalcoholic extracts and the decoction was carried out in a saline medium with recently ecloded microlarvae of *Artemia salina* Leach, in concentrations of 1, 10 and 100 µg/mL. To perform the bioassays, the adapted Fontenele et al. methodology was used. Each solution was assessed in the toxic tests in triplicates, using 10 larvae of *Artemia salina*. This experiment was kept at room temperature (26-28° C.) under artificial lighting for a period of up to 24 hours in a row. A control test was prepared using 5 mL of saline solution with 10 larvae of *A. salina*, under the same experimental conditions of the previously described tests. The results of those bioassays revealed that none of the extracts presented toxicity in concentrations of up to 100 µg/mL.

The microbiological tests were carried out with alcoholic and hydroalcoholic extracts and with the decoction obtained individually from the aerial parts of the 3 species (*S. cayennensis, S. jamaicensis* and *S. elatior*), in concentrations of 2500, 1250, 625, 313 and 156 mg/mL, solubilized into dimethylsulfoxide (DMSO).

The microbiological assays with the referred extracts were carried out in solid medium using the serial dilution art at a ratio of 2, in Sabouraud Dextrose Agar (DIFCO) and Nutrient Agar (Merck). In 12×120 mm test tubes, 3 mL of the medium were added to the $1^{st}$ tube and 1.5 mL to the others; 15 mg of the extract were added to the $1^{st}$ tube, creating the other dilutions. Then, 10 µL of the standardized microorganism suspension were added to $10^6$ CFU, according to tube 0.5 of the McFarland scale, and adjusted to 90% T (530 nm). The extracts were also tested by the Vicent & Vicent and Allegrini arts; the culture medium added with the microorganism suspension was also added filter paper disks (CECO/SP) impregnated with 0.02 mL of each extract. A control was created for each microorganism with standard antimicrobial (chloramphenicol at 30 µg/mL, tetracycline at 30 µg/mL and ketoconazole at 1000 µg/mL). The assays were incubated at 37° C. during 24-48 hours (bacteria and yeast) and room temperature for 10-14 days (filamentous fungi). The microbiological assays of the mentioned products were carried out against gram-positive and gram-negative bacteria; yeast-like fungi and filamentous fungi assays were performed against the following microorganisms: Bacteria: *Bacillus cereus, Escherichia coli, Pseudomonas aeruginosa* and *Staphylococcus aureus*; Yeast-like fungi: *Candida albicans, Candida tropicali* and *Cryptococcus neoforman*; Filamentous fungi: *Aspergillus parasiticus, Penicilium sp* and *Trichophyton rubrum*. The microbiological assays of the mentioned products did not present antimicrobial activity against none of the tested microorganisms.

The pharmacological, pre-clinical and clinical evaluations of the alcoholic extract and the aqueous extracts (decoction) of the aerial parts of *S. cayennensis, S. jamaicensis* and *S. elatior* were individually carried out both in vitro and in vivo for the activities described below.

The assessments were carried out in Swiss-Webster mice (10/group), who received doses of 0.5 and 1.0 mg/Kg of each extract orally. The animals in the control group received saline solution 0.9% (10 mL/Kg; orally) only. This outcome did not produce any death in the groups treated with the alcoholic, hydroalcoholic and aqueous (decoction) extracts of the 3 plant species. Only one group treated with alcoholic extract of *S. elatior* presented a mortality rate of 10%. No evidences of toxicity regarding a significant change to the ponderal evolution, organs weight (heart, spleen, liver, stomach, kidneys, lungs, testicles, ovaries and uterus), hematological and biochemical parameters, were observed among the chronically treated groups and the controls. The results of the tests of acute toxicity evaluations in mice demonstrated that the alcoholic, hydroalcoholic and aqueous (decoction) extracts of the aerial parts of *Stachytarpheta cayensensis, S. jamaicensis* and *S. elatior*, when assessed in different concentrations, individually, did not present toxic effects in oral route in doses of up to 1.0 g/Kg.

From the concentrated aqueous extract (decoction) of the aerial parts of each plant species, a phytotherapic medication was developed. The concentration of the phytotherapic medication per plant was of 60 and 120 mg of the dried extract powder per capsule. A cream for topical use with Lanette base was also developed, using parabenes as preservative and 3% of powder of the aqueous extract of each plant. The recommended posology was 1 capsule 3 times a day, and regarding the cream, 2 daily applications.

Each 280-mg capsule of the phytotherapic medication contains:

| | |
|---|---|
| Dried extract | 60.00 mg |
| Preservative (parabenes) | 0.56 mg |
| Starch | 210.00 mg |
| Water | q. s. |

Each 1.0 mL of the phytotherapic medication contains:

| Dried extract | 3.00 mg |
|---|---|
| Preservative (parabenes) | 0.20 mg |
| Lanette cream (q.s.) | 96.80 mg |

The clinical evaluation of the three phytotherapic medications was performed in 36 adult volunteers (age group ranging 22-53 years old), being 22 women and 14 men, suffering from vitiligo in different stages and extensions, most of them presenting symmetrical unpigmentation and diagnosed based in clinical analyses. The patients were split into three groups of 12 subjects, uncontrolled manner. The patients were initially informed on the research and at that moment every patient was requested urine and blood samples for analysis. At the beginning of the treatment, all patients had their patches photographed and mapped in a transparent paper to record the unpigmented areas and an improved follow-up of the treatment course.

The recommended posology was 1 60-mg capsule of the active ingredient (dried extract) 3 times a day and clinical evaluation once a month. The clinical treatment varied from 14 to 18 months, and for all cases, sunbathing in the morning for 30 to 45 minutes, between 7 and 9 a.m., was recommended. This study did not use placebo and no discontinuation occurred.

It was recorded that all patients had already been subjected to at least one treatment against vitiligo and that more than 60% had already been through more than two treatments. The most used medication was called Viticromim.

The analyses of the results revealed that the three phytotherapic medications achieved positive results, reporting that more than 50% of the patients had their patches repigmented after using the capsules for 18 months in a row. The Group 1, treated with capsules of *Stachytarpheta elatior*, achieved the best relative result when compared against the results of the other groups. The Group 2, treated with capsules of *S. jamaicensis*, presented a result equivalent to Group 3, treated with capsules of *S. cayensensis*. Those results were distributed in the following manner: out of the 21 patients who had their patches repigmented, 9 belonged to the Group 1; 6 patients belonged to Group 2 and the other belonged to Group 3. In this context, it was also recorded that in 6 patients of the Group 1 (50% of the group), the results of observable repigmentation through photographic records and the areas were observed soon after the $4^{th}$ and $5^{th}$ month while using the product. On the other groups, the repigmentation results were reported only after the 6th and the 8th month while using the phytotherapic.

No complaints of malaise, dizziness, headache or vomit were reported for the continuous use of phytotherapic products. Although the repigmentaiton results are partial in 10 patients (27.8%), they were satisfied with the results and only 5 of then considered the results unsatisfactory. The patients who had complete repigmentation of their patches were overjoyed.

Described below are a few examples, with no limitation, of methodologies and arts related to obtention and preparation of fractions, pure compounds from the alcoholic, hydroalcoholic and aqueous extracts of the leaves or aerial parts of *Stachytarpheta cayensensis, S. jamaicensis* and *S. elatior*, appropriate to be used according the invention presented herein.

EXAMPLE 1

Methodology used to obtain alcoholic extract. In a bowl of an extractor equipped with mechanical agitation, add 100 Kg of leaves or aerial parts of the plant (of one of the three mentioned species), dried in ovens with controlled temperature of 60° C. and grounded in electrical mill. Then, add 280 liters of ethanol at 96° GL, with frequent stirring, during 72 to <'> 144 hours (2 to 4 days). After that process, filter the extract in vacuum through 100-µm filters. Using this methodology, a yield of approximately 240 liters of extract solution is obtained. After evaporation of the solvent in rotary evaporator with reduced pressure, a concentrated alcoholic extract is achieved, with the following results per plant, on average: 18% of *Stachytarpheta cayensens;* 16.5% of *Stachytarpheta jamaicensis* and 19.7% of *Stachytarpheta elatior.*

EXAMPLE 2

Methodology used to obtain hydroalcoholic extract. To a stainless steel percolator, add 50 Kg of leaves or aerial parts of the plant (of one of the three mentioned species), dehydrated under shadow over stainless steel nets, during 24 hours. Then, add 80 liters of a hydroalcoholic solution (ethanol:water 1:1) and allow it to percolate for 8 days, with daily and occasional stirring. By the end of the period, filtrate the extract in 100-µm filters and concentrate it in rotary evaporator under reduced pressure. This methodology results in a yield of concentrated hydroalcoholic extract per plant in the following order: 15 to 21% of *Stachytarpheta cayensensis;* 17 to 20% of *Stachytarpheta jamaicensis* and 15 to 22% of *Stachytarpheta elatior.*

EXAMPLE 3

Methodology used to obtain aqueous extract. To obtain the aqueous extract of one of the three *Stachytarpheta* species, add to a percolation bowl with controlled temperature 50 Kg of the leaves of previously selected aerial parts, dried under 65° C. in an oven with forced aeration and, then, ground it in an electric mill. Then, add 100 liters of distilled water to the bowl and heat it to 90° C. for 4 hours in a row. During that period, stir it occasionally. Then, filtrate it using 100-µm filters and, lastly, concentrate the extract (filtrate) in a rotary evaporator under reduced pressure. This extraction process results in the following yields: 7.4 to 11.2% of *Stachytarpheta cayensensis;* 6.5 to 8.9% of *Stachytarpheta jamaicensis* and 7.2 to 11.5% of *Stachytarpheta elatior* in relation to the weight of the vegetable material used in the extraction process.

The invention claimed is:
1. A method for the treatment of vitiligo, comprising administering to a mammal in need thereof one or more pharmaceutical compositions comprising:
   i) about 60 mg of alcoholic, hydroalcoholic, and/or aqueous extracts of one or more parts of Stachytarpheta cayennensis, wherein the extracts comprise a compound with chemical structure I and/or II:

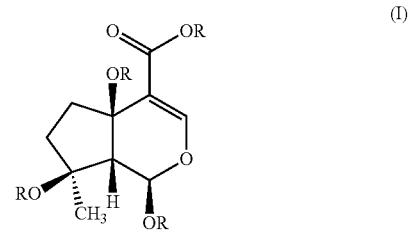

(I)

-continued

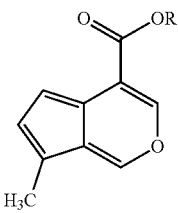

(II)

wherein R is identical or different and each one is independently selected among H, CH$_3$, COCH$_3$, alkali metals, halogens, monosaccharides, disaccharides or polysaccharides, CO(CH$_2$)$_n$CH$_3$, (CH$_2$)$_n$CH$_3$, where n is from 2 to 16; and ii) about 210 mg to about 220 mg of pharmaceutically acceptable excipients.

2. The method of claim 1, wherein the pharmaceutical composition is administered to the mammal at a dosage of about 200 to 400 mg/day.

3. The method of claim 1, wherein the pharmaceutical composition is administered once a day.

4. The method of claim 1, wherein the pharmaceutical composition is administered more than once a day.

5. The method of claim 1, wherein the pharmaceutical composition is administered to the mammal at a dosage of about 60 mg to about 120 mg of dried extract, three times a day.

6. The method of claim 1, wherein the extracts are in the form of a powder.

7. The method of claim 1, wherein the pharmaceutically acceptable excipients comprise parabens and starch.

8. The method of claim 7, wherein each composition comprises about 0.6 mg parabens.

9. The method of claim 7, wherein each composition comprises about 210 mg starch.

10. The method of claim 1, wherein the one or more compositions are each in the form of a capsule.

11. The method of claim 10, wherein the total weight of each capsule is about 280 mg.

12. The method of claim 1, wherein the method comprises orally administering the one or more compositions to the mammal.

13. A method for the treatment of vitiligo, comprising orally administering to a mammal in need thereof one or more pharmaceutical compositions comprising:

i) about 60 mg of alcoholic, hydroalcoholic, and/or aqueous extracts of one or more parts of *Stachytarpheta cayennensis,* wherein the extracts comprise a compound with chemical structure I and/or II:

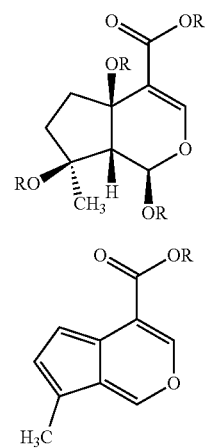

wherein R is identical or different and each one is independently selected among H, CH$_3$, COCH$_3$, alkali metals, halogens, monosaccharides, disaccharides or polysaccharides, CO(CH$_2$)$_n$CH$_3$, (CH$_2$)$_n$CH$_3$, where n is from 2 to 16;

ii) about 0.6 mg parabens; and iii) about 210 mg starch;

wherein each composition is in the form of a capsule having a total weight of about 280 mg.

* * * * *